US012778982B2

(12) United States Patent
Kasurak et al.

(10) Patent No.: US 12,778,982 B2
(45) Date of Patent: Nov. 3, 2026

(54) ANTIOXIDANT NUTRITIONAL SUPPLEMENT FOR IMMUNE SYSTEM SUPPORT

(71) Applicant: VIVA NATURALS, INC., Toronto (CA)

(72) Inventors: Ashley Kasurak, Toronto (CA); Husayn Remtulla, Toronto (CA)

(73) Assignee: Viva Naturals Inc., North York (CA)

( * ) Notice: Subject to any disclaimer, the term of this patent is extended or adjusted under 35 U.S.C. 154(b) by 482 days.

(21) Appl. No.: 18/257,605

(22) PCT Filed: Dec. 14, 2021

(86) PCT No.: PCT/CA2021/051801

§ 371 (c)(1),
(2) Date: Jun. 15, 2023

(87) PCT Pub. No.: WO2022/126255

PCT Pub. Date: Jun. 23, 2022

(65) Prior Publication Data

US 2024/0108650 A1 Apr. 4, 2024

Related U.S. Application Data

(60) Provisional application No. 63/127,074, filed on Dec. 17, 2020.

(51) Int. Cl.

*A61K 33/30* (2006.01)
*A61K 9/48* (2006.01)
*A61K 31/375* (2006.01)
*A61K 31/593* (2006.01)
*A61K 36/185* (2006.01)
*A61K 36/9068* (2006.01)

(52) U.S. Cl.

CPC ............ *A61K 33/30* (2013.01); *A61K 9/4825* (2013.01); *A61K 31/375* (2013.01); *A61K 31/593* (2013.01); *A61K 36/185* (2013.01); *A61K 36/9068* (2013.01)

(58) Field of Classification Search

CPC ................ A61K 31/593; A61K 36/185; A61K 36/9068

See application file for complete search history.

(56) References Cited

U.S. PATENT DOCUMENTS

| | | | | |
|---|---|---|---|---|
| 7,205,010 | B2 | 4/2007 | Sha | |
| 8,257,694 | B2 | 9/2012 | Daikeler et al. | |
| 2005/0249820 | A1 * | 11/2005 | Alam | A61K 8/678 514/474 |
| 2007/0212417 | A1 * | 9/2007 | Cherukuri | A61K 31/375 514/474 |
| 2009/0186012 | A1 * | 7/2009 | Hawkins | A61P 31/16 424/94.63 |
| 2020/0352206 | A1 * | 11/2020 | Wagner-Salvini | A61K 36/062 |

FOREIGN PATENT DOCUMENTS

| | | | | |
|---|---|---|---|---|
| GB | 2562260 | A | 11/2018 | |
| WO | WO-2021260093 | A1 * | 12/2021 | A61K 9/4833 |

OTHER PUBLICATIONS

Prescott, "7 in 1 immune support booster supplement with elderberry, vitamin C and zinc 50 mg, vitamin D 5000 IU, turmeric curcumin & ginger, echinacea—immunity for adults kids, immune defense (120 capsules) $25.12", Dec. 8, 2020, pp. 1-6. ( Year: 2020).*

Small et al., "Instrumentation of an Automatic Capsule-Filling Machine", Apr. 1977, Journal of Pharmaceutical Sciences, vol. 66, No. 4, pp. 504-509. (Year: 1977).*

"Dietary Reference Intakes for Vitamin C, Vitamin E, Selenium, and Carotenoids" The National Academies Press—Science Engineering Medicine, pp. 95 to 185 (2000).

"Estimated Flu-Related Illnesses, Medical visits, Hospitalizations, and Deaths in the United States—2018-2019 Flu Season"; Centers for Disease Control and Prevention, National Center for Immunization and Respiratory Diseases (NCIRD); (https://www.cdc.gov/flu/about/burden/2018-2019.html) Accessed May 29, 2023 (6 pages).

amazon.com, "Viva Naturals elderberry, vitamin C, zinc, vitamin D3 5000 IU & ginger—antioxidant & immune support supplement, 2 month supply (120 capsules)—5 in 1 daily immune support for adults", made public on Aug. 29, 2020 (Aug. 29, 2020), [ online ] [ retrieved on Jan. 21, 2022 (Jan. 21, 2022)]. Retrieved from the Internet.

COVID-19 (https://en.wikipedia.org/w/index.php?title=COVID-19&oldid=988402257). Accessed Nov. 12, 2020 (49 pages).

Herrera, GA, et al., "Influenza vaccine effectiveness among 50-64-year-old persons during a season of poor antigenic match between vaccine and circulating influenza virus strains: Colorado, United States, 2003-2004" vol. 25, Issue 1, Jan. 2, 2007, pp. 154-160.

https://www.fda.gov/media/99069/download. Accessed May 29, 2023 (3 pages).

International Search Report for International Patent Application SN: PCT/CA2021/051801, dated Feb. 9, 2022 (5 pages).

Lein et al., Int J Biomed Sci. Jun; 4(2): 89-96 (2008).

Lushchak, V.L. Free Radicals, Reactive Oxygen Species, Oxidative Stress and Its Classification. Chemico-Biological Interactions, 224, 164 to 175 (2014).

Mar. 22, 2023 Canadian Examiner's Report of Canadian Patent Application SN: 3,154,962 (4 pages).

Natural Health Product—Monograph—"Elder—Sambucus", Health Canada, Jul. 1, 2019 (11 pages).

Natural Health Product—Monograph—"Ginger—Zingiber Officinale", Health Canada, Oct. 30, 2018 (5 pages).

(Continued)

*Primary Examiner* — Michael B. Pallay

(74) *Attorney, Agent, or Firm* — Sand, Sebolt & Wernow Co., LPA

(57) ABSTRACT

The present invention provides methods and compositions for immune support of immune function. The compositions comprise vitamin C; zinc; vitamin D3; elderberry fruit extract; ginger root extract; and at least one excipient. The compositions are effective to neutralize free radicals and to suppress cough and to stimulate the expectoration of mucous.

15 Claims, No Drawings

(56) References Cited

OTHER PUBLICATIONS

Prescott, L., “7 in 1 immune support booster supplement with elderberry, vitamin C and zinc 50mg, vitamin D 5000 JU, turmeric curcumin & Ginger, echinacea—immunity for adults kids, immune defense (120 capsules)”. Dec. 8, 2020 (Dec. 8, 2020), [ online] [retrieved on Jan. 20, 2022 (Jan. 20, 2022)]. Retrieved from the Internet.
Roxas, M. et al. “Colds and Influenza: A Review of Diagnosis and Convention Botanical, and Nutritional Considerations”; Altern Med. Rev. Mar. 12(1): pp. 25 to 48 (2007).
Schwarz, KB “Oxidative Stress During Viral Infection: A Review”; Free Radic Biol Med. 21(5);pp. 641 to 649 (1996).
Viva Naturals, “Elderberry+ Vitamin C + Zinc: 5 in 1 support for a healthy immune system”. made public on Aug. 13, 2020 (Aug. 13, 2020), [ online] [ retrieved on Jan. 20, 2022 (Jan. 20, 2022)]. Retrieved from the Internet: https:/ /vivanaturals.com/products/immunity-support (Publication date of the following document established by Internet Archive Way back Machine (1 page).
Written Opinion for International Patent Application SN: PCT/CA2021/051801, dated Feb. 9, 2022 (5 pages).
Zinc (https://en.wikipedia.org/w/index.php?title=Zinc&oldid=1121871332). Accesed Nov. 15, 2020 (43 Pages).

* cited by examiner

ANTIOXIDANT NUTRITIONAL SUPPLEMENT FOR IMMUNE SYSTEM SUPPORT

FIELD OF THE INVENTION

The instant invention relates to the prevention of free radical damage caused by reactive oxygen species and support of the immune system to help reduce viral infections such as cold, flu, and corona infections. More specifically, the present invention relates to combinations of vitamin C (ascorbic acid); zinc; vitamin D3; elderberry fruit extract; ginger root extract for use in nutritional compositions and methods for neutralizing free radicals, supporting the immune system, promoting cough suppression and stimulating the expectoration of mucous or their symptoms.

BACKGROUND OF THE INVENTION

Flu is a contagious illness caused by the influenza virus. Common flu is characterized by an acute infection associated with respiratory problems, intense muscle pain (myalgia), headaches, chills, nasal obstruction, fever, cough, sneezing and sore throat. The majority of the population will generally recover from flu without any complication. Older people, young children and people with deficient immune systems, may have serious complications or may even die from the flu.

Flu is caused by the influenza virus strain A or B, but strain A is usually the strain responsible for a pandemic flu. There are several strain A subtypes. Influenza A (H1N1) virus is a subtype of influenza A virus and the most common cause of influenza (flu) in humans. Some strains of H1N1 are endemic in humans and cause a portion of all influenza-like illness and of all seasonal influenza. The pandemic H1N1/09 virus is a swine origin Influenza A virus subtype H1N1 virus strain responsible for the 2009 flu pandemic.

New influenza strains infecting humans appear from time to time. These strains frequently originate from other species and have adapted to human through mutations. The swine influenza A H1N1 flu virus, also named Swine Flu, has been reported around the world and was declared a pandemic influenza virus. Swine flu H1N1 originally only affected pigs but started infecting humans in North America in 2009. Humans having little to no natural immunity to this virus and so it can lead to a serious and widespread illness.

Viruses from the influenza family are known to present a high mutation rate and modifications to their genome may occur every single year, resulting in drug resistance.

The CDC estimated that the burden of influenza illness during the 2018-2019 season included an estimated 35.5 million people getting sick with influenza, 16.5 million people going to a health care provider for their illness, 490,600 hospitalizations, and 34,200 deaths from influenza. The number of influenza-associated illnesses that occurred that season was similar to the estimated number of influenza-associated illnesses during the 2012-2013 influenza season when an estimated 34 million people had symptomatic influenza illness. See cdc.gov/flu/about/burden/2018-2019.html accessed Nov. 10, 2020.

Although the overall pathological mechanisms involved in the course of influenza have not been fully elucidated, the ongoing accumulation in the lung of neutrophils and macrophages are thought to play an active role through the production of reactive oxygen species which can ultimately cause and perpetuate tissue injury ("oxidative stress"). Antioxidants have proven to be effective at treating such oxidative stress. See U.S. Pat. Nos. 7,205,010 and 8,257,694 and Schwarz K B. Free Radic Biol Med. 1996; 21(5):641-9 (all of which are incorporated by reference herein in their entirety.)

Vaccines can prevent flu in 70 to 90% of the cases observed in healthy adults (Herrera G A, Vaccine. Volume 25, Issue 1, 2 Jan. 2007, Pages 154-160). However, flu vaccines have to be redesigned each year because the previous year's vaccines are likely to be ineffective against the newly mutated strains. The yearly vaccine is therefore designed before the season begins based on that from the previous year. Since scientists usually cannot predict with accuracy which strain will be dominant, the vaccine may not fully correspond to the new strain. In addition, the flu vaccine is specifically designed against influenza virus strains A and B and does not therefore protect against cold viruses such as rhinovirus and corona types.

Coronavirus disease 2019 (COVID-19) is a contagious respiratory and vascular disease caused by severe acute respiratory syndrome coronavirus 2 (SARS-CoV-2). Symptoms of COVID-19 include fever, cough, fatigue, breathing difficulties, and loss of smell and taste. Long term effects may include severe fatigue, memory loss and other cognitive issues, low grade fever, muscle weakness, and breathlessness. Preventive measures may include social distancing, quarantining, covering coughs and sneezes, and hand washing. There are no proven vaccines or specific treatments for COVID-19 yet, though several are in development. Management involves the treatment of symptoms, supportive care, isolation, and experimental measures. See en.wikipedia.org/wiki/Coronavirus_disease_2019 accessed Nov. 12, 2020.

The common cold is an acute illness and the leading cause of physician visits in the United States (Roxas M, Jurenka J. Colds and influenza: a review of diagnosis and conventional, botanical, and nutritional considerations. Altern Med Rev. 2007 March; 12(1):25-48. PMID: 17397266). It is a leading cause of absence from work, causing an economic burden including loss of productivity and treatment costs. The common cold is caused by a variety of viruses, most of the time of the rhinovirus and corona types. There is currently no cure for a cold and current therapy targets the symptoms. Prevention strategies for the common cold include avoiding infected people and hand washing during cold season.

Inflammation is a central feature of many conditions that are initiated in response to tissue and cellular damage by pathogens, noxious stimuli, such as chemicals and physical injury. Such damage leads to the secretion of mediators such as cytokines as well as activation and migration of immune cells. These mediators add to the generation of excess free radicals such as reactive oxygen species (ROS) which lead to DNA damage. Acute inflammation is a short-term response that results in tissue healing as leukocytes infiltrate the damaged region, removing the stimulus and repairing the tissue. Chronic inflammation, by contrast, is a prolonged, dysregulated and maladaptive response that involves active inflammation and tissue destruction. Such persistent inflammation is associated with many chronic human conditions and diseases, including allergy, atherosclerosis, cancer, arthritis and autoimmune diseases.

Inflammation is currently treated by NSAIDs (non-steroidal anti-inflammatory drugs). Unfortunately, these drugs may lead to blood clots and consequently increase the risk for heart attacks and strokes.

There remains a need for alternative compositions for the prevention and/or treatment of viral infections including corona, cold and flu infections and to prevent free radical damage caused by reactive oxygen species. Natural products are a rich source for discovery of new therapies because of their diversity.

SUMMARY OF THE INVENTION

This invention relates to compositions for immune support comprising an effective combination of: vitamin C; zinc; vitamin D3; elderberry fruit extract; ginger root extract; and at least one excipient wherein the composition is effective to neutralize free radicals and to promote cough suppression and to stimulate the expectoration of mucous.

DETAILED DESCRIPTION OF THE INVENTION

The invention generally relates to drug and nutritional compositions developed from natural sources. More particularly, the invention relates to drug compositions developed from combinations of ginger, vitamin D3, zinc, vitamin C and elderberry extract. Methods of using the drug compositions for the treatment of inflammatory disorders are also within the scope of this invention.

Applicants have developed a unique combination of nutritional supplement ingredients or parts thereof (e.g., their extracts). The combinations of the present invention possess activities which include antioxidant protection against reactive oxygen species as well as immune system support.

The nutritional compositions disclosed herein are useful to reduce oxidative damage in humans by providing the optimal combination and diversity of antioxidants, vitamins and minerals. The nutritional compositions comprise at least one adaptogen. Adaptogens refer to agents which raises the body's nonspecific resistance to various physical, chemical or biological stressors. Adaptogens generally accomplish this by either regulating the activity of hyperfunctioning systems. Ginger and elderberry are both potent adaptogens.

The main active components of the combination of the present invention are ginger root extract, vitamin D3, zinc, vitamin C and elderberry fruit extract.

Accordingly, in one aspect, the present invention presents a composition comprising a combination of ginger, elderberry, vitamin c, zinc, and vitamin D3 for the prevention and/or treatment of cold, flu, and corona infections as well as associated symptoms. The instant invention is effective to neutralizing free radicals, to promote cough suppression and to stimulate the expectoration of mucous.

In a specific embodiment of the composition of the present invention, the composition further comprises a carrier. In another embodiment of the composition of the present invention, the composition comprises a ginger extract and an elderberry extract.

As used herein, and unless the context in which they occur implicitly or explicitly suggest another meaning for these terms, the terms "ginger" refers to the root and rhizome of the plants, parts thereof or extracts thereof. Ginger (*Zingiber officinale*) is also called "warming herb" and has been used for a long time as an important medical herb.

Ginger is generally recognized as safe for human consumption by the German Commission E, (Blumenthal M, 1998) and Health Canada. Health Canada has recognized the use of ginger rhizomes as an expectorant and cough suppressant to help relieve bronchitis as well as coughs and colds. Canadian Natural Health Product Monograph—Ginger—*Zingiber officinale* (Oct. 30, 2018). Rhizomes, are a horizontal underground plant stem capable of producing the shoot and root systems of a new plant. Rhizomes are used to store starches and proteins and enable plants to survive an annual unfavourable season underground.

Ginger has a wide area of usage. Ginger may be preventive against cancer based on its antiviral activity against the Epstein-barr virus. Among the active substances of ginger, 6-gingerol and 6-paradol may be effective in stopping promyelocytic leucaemia by disturbing the DNA synthesis. It supports the cardiovascular system by making the platelets less adherent, this in turn causes a decrease in the problems of circulation system. It is appetizing and can also be used against constipation. In addition to these, it has a warming and sedative effect in cough, flu, cold and other respiratory system diseases.

In another embodiment, the combination comprises concentrated ginger powder. In another embodiment, the ginger extract is a crude ginger extract. In another embodiment, the ginger extract is a crude 100% water ginger extract. In another embodiment, the ginger extract is a $CO_2$ ginger extract. In another embodiment, the ginger extract is a crude ginger extract. In another embodiment, the ginger extract is a crude 100% water ginger extract. In another embodiment, the ginger extract is an alcoholic ginger extract. In another embodiment, the alcoholic ginger extract is a hydroalcoholic ginger extract. In another embodiment, the alcohol used for production of the hydroalcoholic extract comprises a primary alcohol. In another embodiment, the primary alcohol is methanol, ethanol, 1-propanol, 1-butanol or any combination thereof. In another embodiment, the primary alcohol used is ethanol. In another embodiment, the alcohol used for production of the hydroalcoholic extract comprises a secondary alcohol. In another embodiment, a mixture of at least two different alcohols is used. In another embodiment, the alcoholic extract is prepared using a solution comprising between about 20% and about 85% of alcohol. In another embodiment, the extract is prepared using a solution comprising 60% of alcohol. In another embodiment, the extract is prepared using a solution comprising about 30% of alcohol. In another embodiment the ginger extract is an 8:1 concentrated extract. In another embodiment the ginger is a concentrate. In another embodiment the ginger concentrate is an 8:1 concentrate.

Elderberry fruit (as a dry, powder, non-standardized ethanolic extracts (dry extract, tincture, fluid extract)) has traditionally been used in herbal medicine to help relieve symptoms of colds and flus (such as coughs, sore throat and mucus buildup of the (upper) respiratory tract) and it has been approved by Health Canada to relieve the symptoms of colds and flus and as an antioxidant. See Canadian Natural Health Product Monograph—Elder—*Sambucus*—*Sambucus nigra* (Jul. 1, 2019).

In another embodiment, the elderberry extract of the invention is a crude elderberry extract. In another embodiment, the elderberry extract is a crude 100% water elderberry extract. In another embodiment, the elderberry extract is an alcoholic elderberry extract. In another embodiment, the alcoholic elderberry extract is a hydroalcoholic elderberry extract. In another embodiment, the alcohol used for production of the hydroalcoholic extract comprises a primary alcohol. In another embodiment, the primary alcohol is methanol, ethanol, 1-propanol, 1-butanol or any combination thereof. In another embodiment, the primary alcohol used is ethanol. In another embodiment, the alcohol used for production of the hydroalcoholic extract comprises a secondary alcohol. In another embodiment, a mixture of at least two different alcohols is used. In another embodiment, the alcoholic extract is prepared using a solution comprising between about 20% and about 85% of alcohol. In another embodiment, the extract is prepared using a solution comprising 60% of alcohol. In another embodiment, the extract is prepared using a solution comprising about 30% of alcohol. In another embodiment the elderberry fruit extract is a 4:1 concentrated extract.

In another embodiment, the combination comprises a ratio of between about 1:15 and about 10:1 of ginger: elderberry. In another embodiment, the ratio is about 1:5 of ginger:elderberry. In another embodiment, the ratio is about 5:1 of ginger:elderberry. In another embodiment, the ratio is about 3:5 of ginger:elderberry per serving.

In another preferred embodiment the ratio is 1.5 to 5 ginger root (8:1) extract to Elderberry fruit extract (4:1) in a capsule. In a particularly preferred embodiment the capsule is a gelatin capsule.

In another embodiment, the effective serving amount comprises between about 40 mg and about 4500 mg of ginger. In another embodiment, the composition comprises between about 2400 mg and about 3000 mg of ginger root. In another embodiment, the composition comprises between about 100 mg and about 450 mg of ginger 8:1 extract. In another embodiment, the composition comprises between about 300 mg and 360 mg of ginger 8:1 extract. In another embodiment, the composition comprises between about 300 mg and 360 mg of ginger 8:1 concentrate.

In a particularly preferred embodiment each capsule contains about 150 mg of ginger root (8:1) extract and about 500 mg of Elderberry fruit (4:1) extract.

In another embodiment, the effective serving amount comprises between about 40 mg and about 5000 mg of elderberry. In another embodiment, the composition comprises between about 3000 mg and about 5000 mg of elderberry fruit. In another embodiment, the composition comprises between about 500 mg and about 1500 mg of elderberry 4:1 extract. In another embodiment, the composition comprises between about 1000 mg and 1200 mg of elderberry 4:1 extract.

Vitamin D3 or cholecalciferol is approved by Health Canada for the support of immune function among other things. It is found in food such as some fish, beef liver, eggs, and cheese. Certain foods such as milk, fruit juice, yogurt, and margarine also may have cholecalciferol added to them in some countries including the United States. Dietary reference intake values for vitamin D (cholecalciferol and/or ergocalciferol) have been established and recommendations vary depending on the country. In the US: 20 μg/d (800 IU per day) for all individuals between the ages of 1 and 70 years old, inclusive. In the EU: 20 μg/d (800 IU per day). In France: 25 μg/d (1000 IU per day) See fda.gov/media/99069/download accessed Dec. 6, 2020.

In certain embodiments, compositions of the instant invention include about 4000 IU (100 μg) of vitamin D3 to about 8,250 IU (210 μg) per serving. In additional embodiments, 5000 IU (125 μg) to about 8,250 IU (210 μg) are included per serving.

A preferred embodiment comprises about 3247 IU of vitamin D3 per capsule.

A preferred embodiment comprises about 3.82 mg of vitamin D3 (850,000 IU per g) per capsule.

Vitamin C, also known as ascorbic acid and ascorbate, is a vitamin found in various foods and sold as a dietary supplement. It is used to prevent and treat scurvy. Vitamin C is an essential nutrient involved in the repair of tissue and the enzymatic production of certain neurotransmitters. It is required for the functioning of several enzymes and is important for immune system function. It also functions as an antioxidant.

In 2000 the North American Dietary Reference Intake chapter on vitamin C updated the Recommended Dietary Allowance to 90 mg/day for adult men and set a tolerable upper intake level for adults of 2,000 mg/day. See Dietary Reference Intakes for Vitamin C, Vitamin E, Selenium, and Carotenoids. Washington, DC: The National Academies Press. 2000. pp. 95-185. Embodiments of the instant invention include 300 mg to 800 mg of vitamin C per serving. Additional embodiments include 400 mg to 600 mg of vitamin C per serving.

A preferred embodiment comprises about 221 mg of vitamin C (95%) per capsule.

Embodiments of the present invention include zinc oxide as a source of the element zinc. In other embodiments of the invention, zinc may be included in such forms as zinc acetate, or zinc gluconate, zinc sulfate, zinc citrate, zinc gluconate and zinc picolinate.

Zinc supplements (frequently zinc acetate or zinc gluconate lozenges) are used as dietary supplements for the treatment of the common cold. The use of zinc supplements at doses in excess of 75 mg/day within 24 hours of the onset of symptoms has been shown to reduce the duration of cold symptoms by about 1 day in adults. See //en.wikipedia.org/wiki/Zinc#Dietary_supplement, accessed on Nov. 15, 2020.

Embodiments of the instant invention include 5 mg to 30 mg of zinc. Additional embodiments include 10 mg to 20 mg of zinc per serving.

A preferred embodiment comprises about 6.6 mg of 80% zinc oxide per capsule.

A combination of these two plants (or specific parts or extracts thereof) elements, and vitamins according to the invention provide an alternative way of attenuating/alleviating cold, flu and corona symptoms and/or decreasing the duration of the infection period.

In another embodiment of the composition of the present invention, the combination prevents or treats at least one of the following symptoms: the viral titer in the subject's blood or cells, runny nose, plugged nose, sneezing, sore throat, scratchy throat, cough, hoarseness, head congestion, chest congestion, exhaustion, fever, muscle pain, loss of appetite, headache and chills. In another embodiment, the combination prevents or treats at least two of the symptoms. In another embodiment, the combination of the present invention prevents, treats, or reduces at least 2 of the above symptoms. In one embodiment the compositions of the invention are effective for neutralizing free radicals, promoting cough suppression and stimulating the expectoration of mucous or their symptoms.

In another embodiment of the composition of the present invention, the composition is for use in the prevention and/or treatment of cold and/or flu infection. In another embodiment, the combination prevents and/or treats the cold and/or flu infection synergistically. In another embodiment, the composition is for use in the prevention and/or treatment of an influenza infection. In another embodiment, the composition is for use in the prevention and/or treatment of a rhinovirus infection. In another embodiment, the composition is for the prevention of cold and/or flu infections. In another embodiment, the composition is for the treatment of cold and/or flu infections. In another embodiment, the composition is adapted for a veterinary application. In another embodiment, the composition is adapted for humans.

In another aspect, the present invention provides a method of preventing and/or treating a cold and/or flu infection in a subject in need thereof comprising administering to the subject an effective amount of a composition comprising a combination of ginger and elderberry, whereby the cold, flu or corona infection is prevented or treated.

In one embodiment the composition according to the present invention is administered daily to prevent viral infection and neutralizing free radicals. Chronic oxidative stress is defined as "Oxidative stress is a situation when steady-state ROS concentration is transiently or chronically enhanced, disturbing cellular metabolism and its regulation and damaging cellular constituents" (see Lushchak, V. Chemico-Biological Interactions 224 (2014) 164-175 and Lien, A. et al, Int J Biomed Sci. 2008 June; 4(2): 89-96; both incorporated in their entirety herein by reference). Numerous pathologies such as cancer, diabetes mellitus, cardiovascular and neurodegenerative diseases exemplify the chronic oxidative stress.

In another embodiment of the method of the present invention, the composition is administered within 48 h of the onset of cold or flu symptoms. In another embodiment, the composition is administered within 24 h of the onset of cold or flu symptoms. In another embodiment, the composition is administered twice daily.

In a further aspect, the present invention concerns the use of a composition comprising a combination of ginger and elderberry for the manufacture of a composition of the present invention for preventing or treating a cold or flu infection. In an embodiment, the use is for the manufacture of a medicament. In another embodiment, the use is for the manufacture of a nutraceutical or dietary composition (e.g., a food supplement or dietary supplement).

In a further aspect, the present invention concerns the use of the composition as defined above, for the prevention and/or treatment of a cold and/or flu infection or in the manufacture of a medicament, nutraceutical composition or dietary composition for the prevention and/or treatment of a cold and/or flu infection.

In one aspect of the invention, it is important to achieve a capsule manufacturing process that allows for a maximum of two capsules per serving in order to allow users a reasonable dosage form while still obtaining the full benefits of the novel formulations according to the invention and providing an efficient encapsulation manufacturing process. Numerous methods fail to achieve these ends with the efficacious compositions according to the invention requiring novel manufacturing solutions.

In a further aspect, the present invention concerns the efficient manufacture of capsules containing the compositions of the invention. In certain preferred embodiments, the invention comprises granular vitamin C rather than powdered in order to increase the density of the formula and allow for a two capsule serving.

In certain preferred embodiments, the manufacturing process according to the invention comprises forming powder slugs for encapsulation. Such methods make use of, for example, a tamping-style capsule filler to create uniform powder slugs in a process that uses a dosing bowl, product bed, tamping pins, and a dosing disc in order to increase the density of the formula and allow for a two capsule serving. Such methods and functionally similar alternative methods are known in the art. In a particularly preferred embodiment, the ginger and elderberry powders are mixed and slugged together. In another particularly preferred embodiment, the ginger and elderberry powders are mixed and slugged together twice.

In another preferred embodiment the formulation is slugged twice.

In another aspect, the invention comprises the use of gelatin capsules rather than vegetable-based capsules because of the dry nature of the formulation and the resulting vegetable capsule chipping and cracking.

EXAMPLES

Example 1

Active Ingredients: Per One (1) Capsule—Two Capsules Provide an Effective Serving

| | |
|---|---|
| ELDERBERRY (fruit) 4:1 EXTRACT (*Sambucus nigra*) | 500.00 mg |
| VITAMIN C (as ASCORBIC ACID 99%) | 202 mg |
| GINGER (root) (from 8:1 concentrate) (*Zingiber officinale*) | 150 mg |
| ZINC OXIDE (79.5% Zn) | 6.25 mg |
| VITAMIN D3 (as Cholecalciferol) | 62.5 ug |

Excipients: Per One (1) Capsule—Two Capsules Provide an Effective Serving

| | |
|---|---|
| DICALCIUM PHOSPHATE | 86 mg |
| VEGETABLE STEARATES | 39 mg |
| SILICON DIOXIDE | 18 mg |
| CLEAR/CLEAR GELATIN CAPSULE | 130 mg |

Example 2

Active Ingredients: Per One (1) Capsule—Two Capsules Provide an Effective Serving

| | |
|---|---|
| ELDERBERRY (fruit) 4:1 EXTRACT (*Sambucus nigra*) | 500 mg |
| VITAMIN C (as ASCORBIC ACID 99%) | 200 mg |
| GINGER (root) (from 8:1 concentrate) (*Zingiber officinale*) | 150 mg |
| ZINC OXIDE (91% Zn) | 5 mg |
| VITAMIN D3 (as Cholecalciferol) | 62.5 ug |

Excipients: Per One (1) Capsule—Two Capsules Provide an Effective Serving

| | |
|---|---|
| DICALCIUM PHOSPHATE | 1.0 mg |
| VEGETABLE STEARATES | 47.52 mg |
| SILICON DIOXIDE | 10 mg |
| CLEAR/CLEAR GELATIN CAPSULE | 130 mg |

Example 3

Active Ingredients: Per One (1) Capsule—Two Capsules Provide an Effective Serving

| | |
|---|---|
| ELDERBERRY (fruit) 4:1 EXTRACT (*Sambucus nigra*) | 500.00 mg |
| VITAMIN C (as ASCORBIC ACID 95%) | 221.05 mg |
| GINGER (root) (from 8:1 concentrate) (*Zingiber officinale*) | 150 mg |
| ZINC OXIDE (79.5% Zn) | 6.60 mg |
| VITAMIN D3 (as Cholecalciferol)(850 000 IU/g) | 3.82 mg |

Excipients: Per One (1) Capsule—Two Capsules Provide an Effective Serving

| | |
|---|---|
| DICALCIUM PHOSPHATE | 1 mg |
| VEGETABLE STEARATES | 47.52 mg |
| SILICON DIOXIDE | 10 mg |
| CLEAR/CLEAR GELATIN CAPSULE | 130 mg |

Other objects, advantages and features of the present invention will become more apparent upon reading of the following non-restrictive description of specific embodiments thereof, given by way of examples only with reference to the accompanying drawings.

Upon reading this specification, the skilled artisan will recognize that numerous additions, revisions, permutations and modifications are possible, while still remaining within the practice of the invention described herein. Such additions, revisions, permutations and modifications are part of the present invention.

The invention claimed is:

1. A composition for immune support comprising:
- vitamin C;
- zinc;
- vitamin D3;
- elderberry fruit extract;
- ginger root extract;
- at least one excipient wherein the composition is effective to neutralize free radicals and to suppress cough and to stimulate the expectoration of mucous; and
- wherein the composition is encapsulated in a non-vegetable-based capsule.

2. The composition of claim 1 wherein the elderberry is *Sambucus nigra.*

3. The composition of claim 1 wherein the ginger is *Zingiber officinale.*

4. The composition of claim 1 comprising as active ingredients by weight of:
- about 20% to 32% ascorbic acid;
- about 0.2% to 2% zinc oxide;
- about 0.005% to 0.01% vitamin D3;
- about 55% to 65% elderberry fruit extract; and
- about 15% to 25% ginger root extract.

5. The composition of claim 4, further comprising at least one excipient selected from the group consisting of dicalcium phosphate, vegetable stearates, and silicon dioxide.

6. The composition of claim 1 comprising as active ingredients per serving by weight of:
- about 400 mg to 600 mg of ascorbic acid;
- about 10 mg to 20 mg zinc oxide;
- about 125 μg to 210 μg of vitamin D3;
- about 1000 mg to 1200 mg of elderberry fruit extract; and
- about 300 mg to 360 mg ginger root extract.

7. The composition of claim 1 comprising as active ingredients per serving by weight of:
- about 10 mg to 1500 mg elderberry fruit extract;
- about 5 mg to 450 mg ginger root extract;
- about 300 mg to 800 mg ascorbic acid;
- about 5 mg to 36 mg zinc oxide; and
- about 0.003 mg to 10 mg vitamin D3.

8. The composition of claim 1 comprising as active ingredients per serving by a weight percent of:
- about 2.8% to 65% elderberry fruit extract;
- about 1.4% to 20% ginger root extract;
- about 28% to 93% ascorbic acid;
- about 0.7% to 1.78% zinc oxide; and
- about 0.0008% to 0.36% vitamin D3.

9. The composition of claim 1 wherein the non-vegetable-based capsule is a bovine-sourced gelatin capsule.

10. A method of manufacturing the composition of claim 1 comprising:
- compacting the ginger and elderberry extracts;
- providing powdered vitamin C; and
- encapsulating the composition in bovine gelatin capsules.

11. A composition for immune support comprising:
- vitamin D3;
- elderberry fruit extract;
- ginger root extract;
- at least one excipient wherein the composition is effective to neutralize free radicals and to suppress cough and to stimulate the expectoration of mucous; and
- wherein the composition is encapsulated in a non-vegetable-based capsule.

12. The composition of claim 11 wherein the non-vegetable-based capsule is a bovine-sourced gelatin capsule.

13. The composition of claim 11 wherein the elderberry and ginger extracts are mixed and slugged together one or more times.

14. The composition of claim 11 wherein capsules are manufactured using vitamin C in a granular form.

15. A method of manufacturing the composition of claim 11 comprising:
- compacting the ginger and elderberry extracts, the composition further comprising:
  - providing powdered vitamin C; and
  - encapsulating the composition in bovine gelatin capsules.

* * * * *